(12) United States Patent
Letort et al.

(10) Patent No.: US 7,274,960 B2
(45) Date of Patent: Sep. 25, 2007

(54) METHOD AND APPARATUS FOR TREATING ANEURYSMS BY ELECTROSTIMULATION

(75) Inventors: Michel Letort, Prevessins (FR); Jeff Elkins, Woodside, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 548 days.

(21) Appl. No.: 10/911,973

(22) Filed: Aug. 5, 2004

(65) Prior Publication Data
US 2006/0030887 A1    Feb. 9, 2006

(51) Int. Cl.
*A61N 1/00* (2006.01)
(52) U.S. Cl. .......................................... 607/2
(58) Field of Classification Search ................ 607/2, 607/44, 50, 63, 72
See application file for complete search history.

(56) References Cited

U.S. PATENT DOCUMENTS

| | | | |
|---|---|---|---|
| 4,809,697 A | 3/1989 | Causey, III et al. | |
| 4,944,299 A | 7/1990 | Silvian | |
| 5,398,687 A | 3/1995 | Abell | |
| 5,690,691 A * | 11/1997 | Chen et al. | 607/40 |
| 5,861,014 A | 1/1999 | Familoni | |
| 6,216,039 B1 | 4/2001 | Bourgeois | |

FOREIGN PATENT DOCUMENTS

EP    1078649    2/2001

* cited by examiner

*Primary Examiner*—Mark Bockelman
(74) *Attorney, Agent, or Firm*—Forrest Gunnison

(57) ABSTRACT

An aneurysmal sac arterial wall electrostimulation system (11) comprises an array of electrical leads (4 and 5) placeable in contact with a portion of the arterial wall (12) to be electrostimulated and a source (3) of electrostimulation attached to the array of electrical leads. The source provides periodic electrostimulus to at least one of the array of leads in accordance with a treatment program and at least one of the array of leads senses the contraction condition of the aneurysmal sac arterial wall (10) which is provided as a feedback loop input signal to the treatment program. Repeated electrostimulation of a vascular passage using the system (11) provides increased muscle tone or pseudo permanent contraction of such vascular passage.

11 Claims, 7 Drawing Sheets

72 — IMPLANTING LEADS TO PROVIDE STIMULATION INDUCING THE CONTRACTION OF THE ANEURYSMAL SAC ARTERIAL WALL

→

74 — ELECTRICALLY STIMULATING THE LEADS ACCORDING TO A TREATMENT PROGRAM

→

76 — SENSING A CONTRACTION CONDITION OF THE ANEURYSMAL SAC, PREFERABLY BY EMITTING A STIMULATION PULSE TRAIN AT A PREDETERMINED RATE SUITABLE FOR THE ANEURYSMAL SAC ARTERIAL WALL

→

78 — ADJUSTING THE TREATMENT PROGRAM BASED ON THE INFORMATION RECEIVED FROM THE STEP OF SENSING THE CONTRACTION CONDITION, PREFERABLY TO PREVENT OVER-STIMULATION OR OVER-CONTRACTION OF THE ANEURYSMAL SAC ARTERIAL WALL.

METHOD AND APPARATUS FOR TREATING ANEURYSMS BY ELECTROSTIMULATION

FIELD OF THE INVENTION

This invention relates generally to electrostimulation, and more particularly to treatment of aneurysmal sacs using electrostimulation.

BACKGROUND OF THE INVENTION

One common reason aneurysmal sacs occur is attributed to the weakening of the arterial wall. Common treatment or medical procedures used to bolster the arterial wall include complicated surgery to open the abdomen and replace a portion of the artery with a graft, or alternately using a stent-graft system to provide endovascular exclusion of abdominal aortic aneurysm (AAA) (or of thoracic aortic aneurysm (TAA)).

In the process of endoluminal AAA repair using a stent-graft deployment system, a balloon catheter can be used to appropriately seat the graft in a target area. In general, the use of stent-grafts for treatment or isolation of vascular aneurysms and vessel walls which have been weakened by disease (endoluminal repair) are well known. Intraluminal deployment is typically effected using a delivery catheter with coaxial inner (guidewire or balloon catheter) and outer (sheath) tubes arranged for relative axial movement. The stent-graft is compressed and disposed within the distal end of an outer catheter tube and blocked from the sliding away from the tip by the inner tube or a structure connected to the inner tube. The catheter is then maneuvered, typically routed though a lumen (e.g., vessel), until the end of the catheter (and the stent-graft) is positioned in the vicinity of the intended treatment site. To avoid "endoleaks" during initial placement of the stent-graft, the balloon catheter can be used to appropriately seat the stent-graft with the blood vessel wall or walls. It should also be noted that endoleaks can also occur after endovascular exclusion of AAA/TAA since the arterial wall is subject to a drop in muscular resistance as evidenced by the lower resistance of the aneurysmal sac to rupture.

Therefore, a need exists to bolster or strengthen the arterial walls of an aneurysmal sac to counteract the weakening described above.

SUMMARY OF THE INVENTION

In a first aspect according to the present invention, an aneurysmal sac arterial wall electrostimulation system comprises an array of electrical leads placeable in contact with a portion of the arterial wall to be electrostimulated and a source of electrostimulation attached to the array of electrical leads. The source of electrostimulation provides periodic electrostimulus to at least one lead in the array of leads in accordance with a treatment program. At least one lead in the array of leads senses the contraction condition of the aneurysmal sac arterial wall and provides a feedback loop input signal back to the treatment program.

In a second aspect according to the present invention, a method for providing electrostimulation to an aneurysmal sac arterial wall comprises the steps of implanting leads to provide stimulation inducing the contraction of the aneurysmal sac arterial wall and electrically stimulating the leads according to a treatment program. The method further includes the steps of sensing a contraction condition of the aneurysmal sac and adjusting the treatment program based on information received from the step of sensing the contraction condition. In this manner, the vessel walls of the aneurysmal sac are strengthened to increase the chances of success of an endoluminal repair or possibly obviate the need for such procedures.

BRIEF DESCRIPTION OF THE DRAWINGS

The invention recited in the claims and other aspects according to the present invention may be better understood and appreciated with reference to specific embodiments according to the invention, when read in conjunction with the accompanying drawings, wherein:

FIG. 7 is a flow chart illustrating the steps of a method in accordance with the present invention.

DETAILED DESCRIPTION OF THE DRAWINGS

Electrical stimulation of the arterial muscles bolsters or at least maintains the muscular capacity and integrity of the artery. Conceptually, such treatment can reinforce the arterial wall providing greater sac integrity and control of sac pressure. Sac pressure results from the flow of blood pumped by the heart through the artery and sac. Ideally, this treatment will further diminish the need or obviate the use of a stent-graft or other treatment of AAA. As a preventative measure, this electrostimulation treatment can prevent rupture of the artery in the case of AAA or can act as a first step in the treatment thereof before deploying an endograft. Ideally, this treatment could be used to reverse the degeneration of the elastic or collagen components of the arterial wall, to thereby reverse the expansion of an aneurysmal sac.

Figure 1:
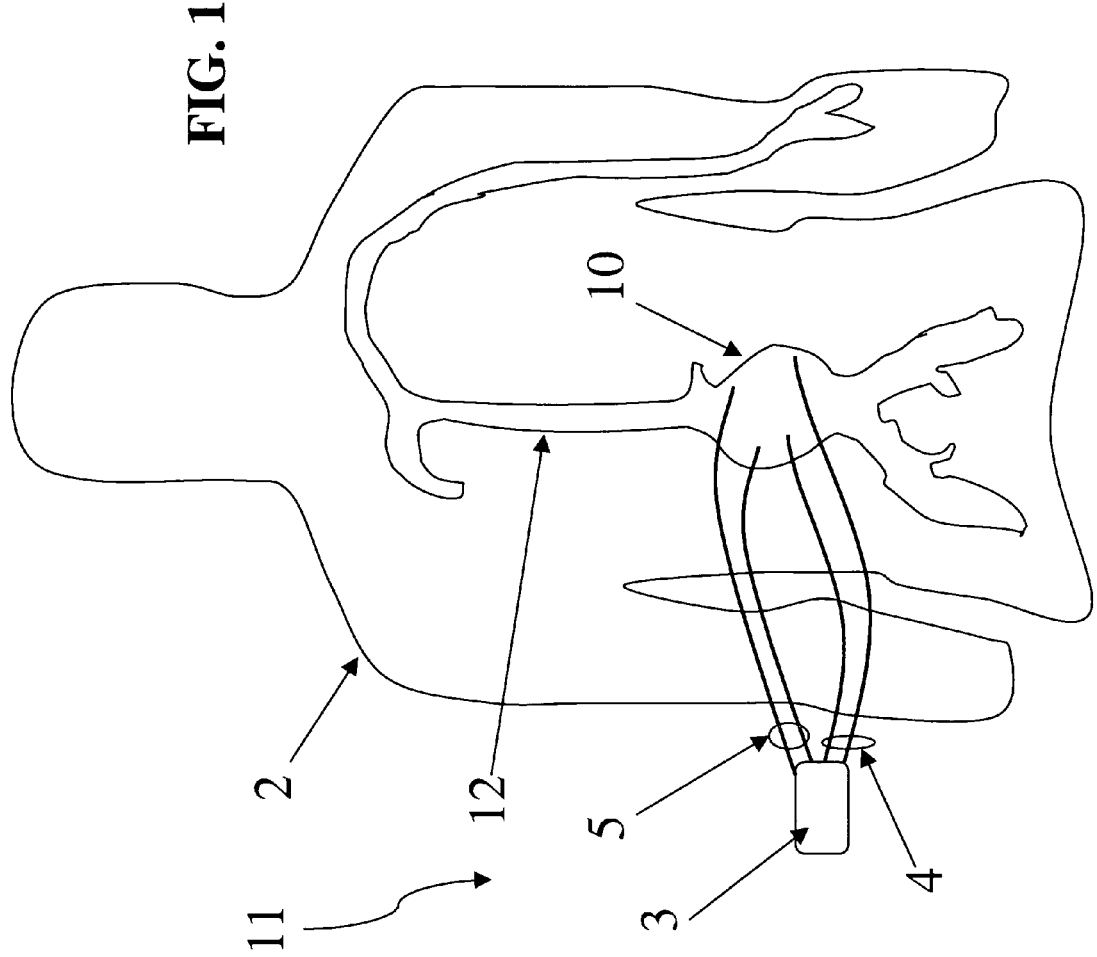
FIG. 1 depicts a schematic diagram of an apparatus implanted within a patient in accordance with the present invention.

FIG. 1 shows a system 11 implanted in a patient 2. As seen, the system 11 can comprise an implantable or external pulse generator 3 featuring two or more sets of leads 4 and 5 having electrodes which are coupled to a portion of an arterial wall 10 of an artery 12. The electrodes can be stimulated sequentially by pairs (not as single pairs), therefore increasing the distance between electrodes and the distribution of stimulation. A portion of the arterial wall 10 is diseased and weakened by an aneurysm such as an abdominal aortic aneurysm. The first set of leads 4 provides stimulation to a muscular portion of the arterial wall 10. If multiple leads and corresponding electrodes are used for stimulation as mentioned above, then the electrodes can be stimulated sequentially by pairs (but not with a single pair) to increase the distribution of stimulation to a larger area. The second set of leads 5 provide sensing of the contraction condition of the arterial wall portion 10 to the pulse generator 3. In one embodiment, the pulse generator 3 is implanted within the patient 2. As such, the implantable pulse generator 3 features a hermetic enclosure, as is well known in the art. The leads used for both the first set 4 and the second set 5 may be any acceptable lead. In the embedded embodiment, the preferred leads are Medtronic Model No. 4300 intramuscular lead. Of course, other configurations of leads or lead systems may be used, including the use of only a single lead, a single set of leads (i.e. two), or even the use of three or more sets of leads. Moreover, although shown as being coupled to the arterial wall portion 10, this same device and method may be used along or on any of the other vascular structures subject to weakened wall muscles, including other portions of the aortic artery.

The first set of leads 4 are stimulation leads which conduct stimulation pulses from the pulse generator 3 to the arterial wall portion 10. First set of leads 4 is preferably implanted at an inner surface (endoluminal electrode), or at the outer surface to connect the electrode with the media or adventicia layer of the artery. Of course, other locations for first set of leads 4 may be used, such as the tunica media layer of the artery. The second set of leads 5 are sensing leads which conduct any activities sensed (muscle contractions or changes in muscle mass or density) in the arterial wall portion 10 to the pulse generator 3. Preferably the second set of leads 5 are positioned in locations similar to the initial set of leads, although these leads may also be positioned in other locations.

Figure 2:
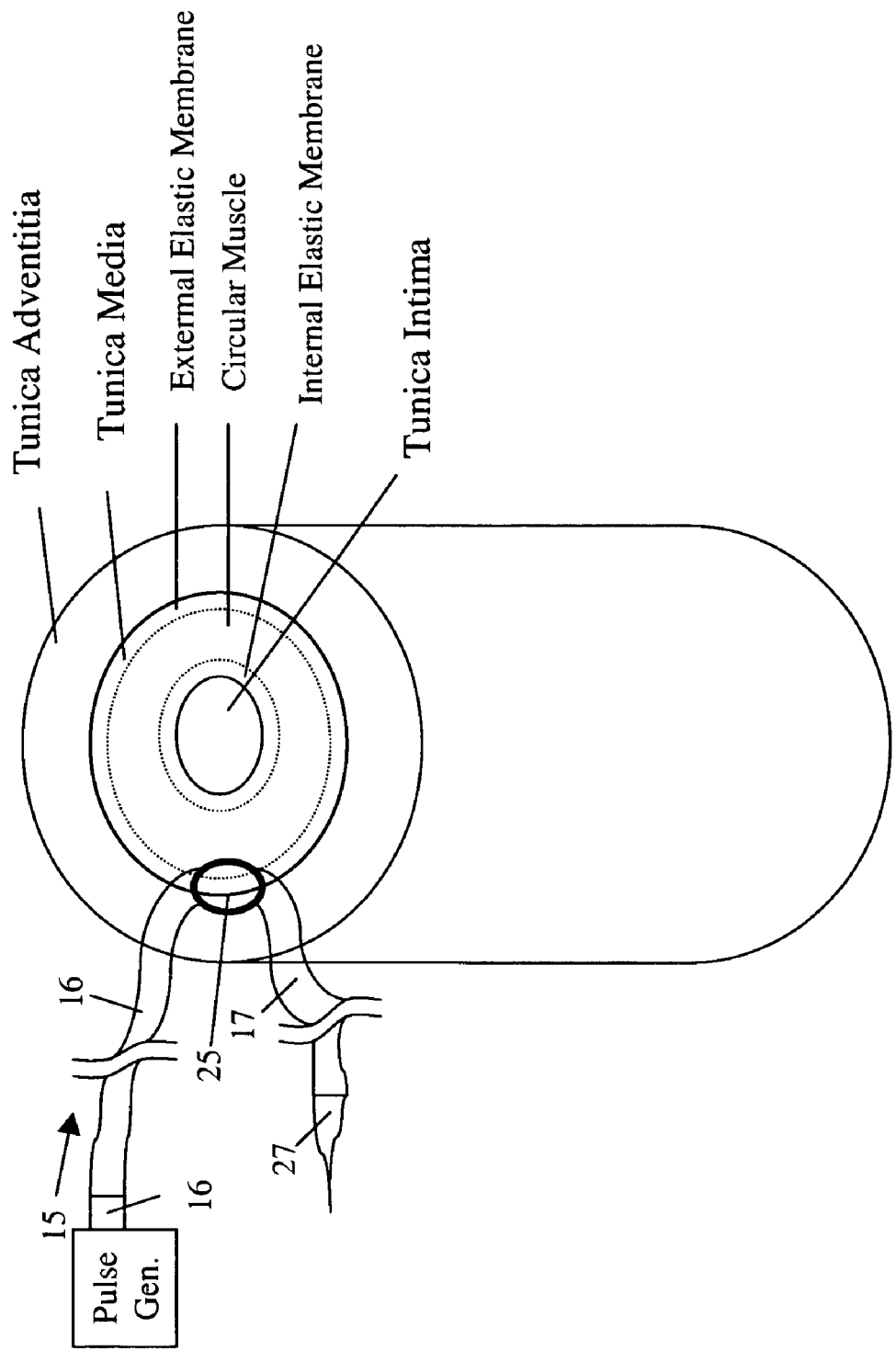
FIG. 2 depicts a detailed cross sectional view of the artery muscle showing an electrode of a lead of FIG. 1 implanted.

FIG. 2 shows the positioning of an electrode of a lead within the various layers of the arterial wall portion 10. As seen, the arterial wall portion 10 has essentially three layers of tissue, namely the tunica adventitia, the tunica media, and the tunica intima. The tunica adventitia is the strong outer covering of arteries. It is composed of connective tissue as well as collagen and elastic fibers. The tunica media is composed of smooth muscle cells and elastic fibers. In particular, the tunica media includes an outer elastic layer, a circular muscle layer and an inner elastic layer. The tunica intima is a layer composed of an elastic membrane lining and smooth endothelium that is covered by elastic tissues. In one embodiment, the electrode of a lead can be in contact with and partially positioned into the tunica adventitia and the circular muscle layer of the tunica media of the arterial wall portion as shown in FIG. 2. This may be important in that intramuscular electrodes may effectively stimulate the arterial wall with less energy than may be required for surface electrodes used on an exterior layer such as the tunica adventitia alone. Of course, other types of electrodes or lead systems may be used, including those which contact only any one of each of the layers of the arterial wall. Moreover, although in one embodiment a pair of unipolar leads are used for stimulation and a second pair of unipolar leads are used for sensing, other configurations of leads may be used, such as bipolar, tripolar, quadrapolar, as well as any other configuration suitable, such as a unipolar lead and can.

Figure 3:
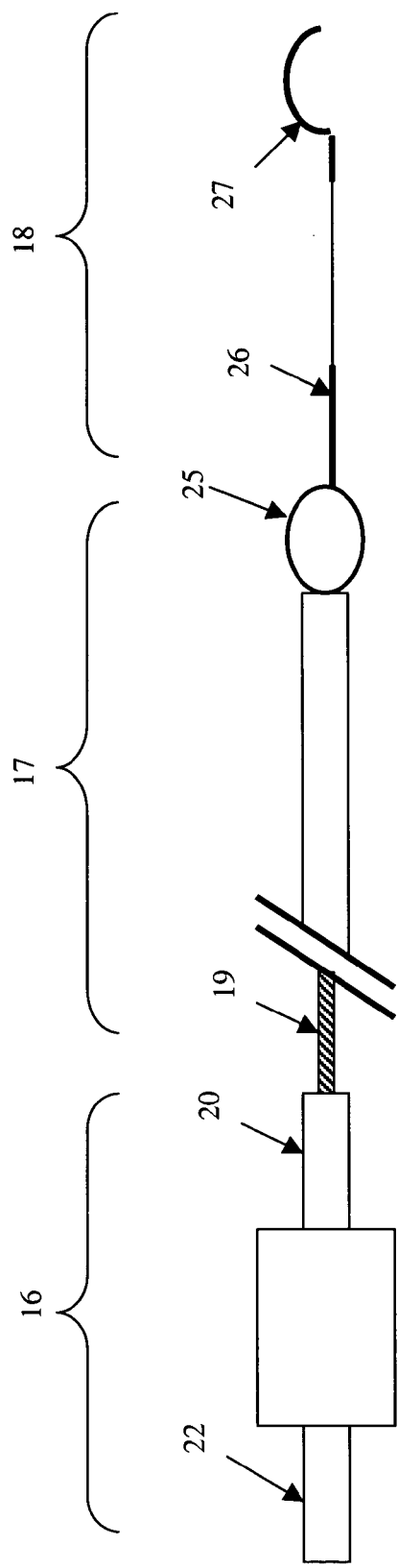
FIG. 3 depicts a plan view of a lead used with an apparatus in accordance with the present invention.

FIG. 3 is a plan view of an exemplary lead 15. As seen, the lead 15 has three sections, connector section 16, body section 17 and fixation section 18. Connector section 16 includes a connector pin 22 to electrically couple the lead 15 into the pulse generator. Any connector pin 22 known in the art may be used. Body section 17 includes an electrical conductor 19 surrounded by an electrical insulator 20. In one embodiment electrical conductor 19 is a platinum iridium alloy and electrical insulator 20 is silicone. Of course, other biocompatible materials may also be used. At the distal end of the body section 17 is an electrode 25. Electrode 25 is a polished platinum iridium alloy. Other materials having comparable characteristics may be used, such as a porous platinized structure. In addition, the electrode 25 could further feature various pharmaceutical agents, such as dexamethasone sodium phosphate or beclomethasone phosphate to minimize the inflammatory response of the tissue to the implanted lead 15. Other agents such as antibiotics may also be used.

Located distal to the electrode 25 is the fixation section 18. As seen, fixation section 18 has two pieces, a suture 26 which is coupled to a needle 27. Needle 27 is preferably curved. In another embodiment such a suture may feature a fixation coil, as is well known in the art, to cooperate with the body tissue after implantation to maintain the electrode at the location where it was implanted. Of course, other fixation mechanisms may be used, such as fixation discs, as is well known in the art.

Figure 4:
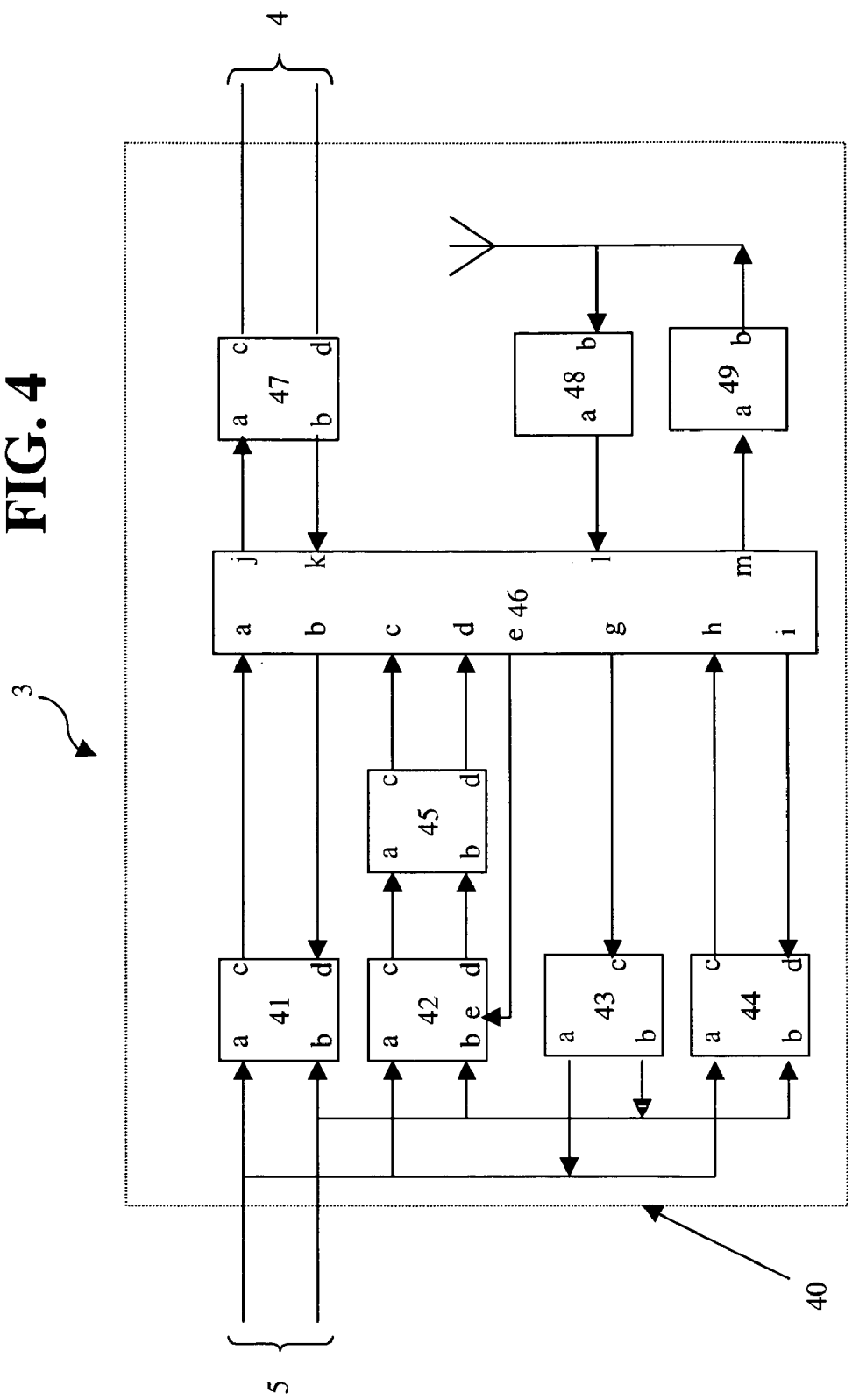
FIG. 4 is a functional block diagram of the electrostimulation system in accordance with the present invention.

FIG. 4 is a functional block diagram of a pulse generator according to the present invention. Pulse generator 3 is preferably enclosed by a hermetic enclosure 40 encapsulating the electronics and battery while the device is implanted. The hermetic enclosure 40 may be of any suitable construction, for example, similar to those used for heart pace makers.

Pulse generator 3 is connected to two sets of leads 4, 5 which are, in turn, implanted in the arterial wall portion. The first set of leads 4 transmits stimulation pulses from pulse generator 3 to the arterial wall portion. The second set of leads 5 provide sensing of the activity of the arterial wall portion 10 to the pulse generator 3. Although in this embodiment the stimulating leads and sensing leads are separate leads, using a combination of leads may also be employed, which both sense and stimulate.

Also coupled to the sensing electrodes 5 is an AC current generator 43. This AC current generator 43 is part of a plethysmorgraphy circuit. Overall, the plethysmography circuit is present to provide a means for sensing mechanical activity of the underlying tissue. That is, whereas the spike activity in the sensed signal may be used to sense contraction, the contraction may also be sensed using the plethysmography circuit. Plethysmography circuit is comprised from AC current generator 43, amplifier, modulator and ADC converter 44 as well as a portion of the microprocessor 46. The AC current generator 43 is switched on via signal from microprocessor 46 once a slow wave is detected or a pacing stimulus is emitted. It can be switched off roughly 10 seconds after being switched on also from the same line or signal from the microprocessor 46. The AC current generator 43 amplitude and frequency are programmable via microprocessor 46. The frequency should be such that it is not detected by amplifiers 41, 42, 45, e.g., 1 kHz. If synchronous detection by amplifier 41 occurs at the end of the blanking period, then the amplitude and/or the frequency of the AC current generator 43 is adjusted by the microprocessor 46 to avoid subsequent detection of the generated AC current.

Turning now to the amplifier, the modulator and ADC converter 44, the AC voltage caused by the injection of AC current generator 43 is amplified and demodulated and converted to detect impedance changes caused by contractions of the underlying tissue. The ADC converter digitizes the amplitude of the demodulated signal. The digitized signal is transmitted via line 44*c*-46*h* to the microprocessor 46. The microprocessor 46 analyzes the signal pattern by comparing it with one or more templates to identify it as a contraction as well as to reject interference or signals generated by postural changes or vomiting. This template comparison is done synchronously to the detection of the slow wave. Line 46*i*-44*d* is used to control the amplifier and ADC from the microprocessor 46.

The microprocessor 46 handles all timings and data storage of the pulse generator and may be of any suitable design. A microprocessor 46 such as that used in the Thera I series of Medtronic pacemakers is used. The description of the microprocessor 46 function is described in the section below which details the operation of the algorithm used.

Stimulation pulses are generated by the output stage 47. In one embodiment, the output stage 47 generates pulse trains. It should be understood many types of pulse trains or stimulation pulses might be used including constant current or constant voltage outputs, or a mixture of both. The output pulses are transported to the arterial wall tissue via medical electrical leads 4.

Turning again to the output stage 47, when an output pulse is to be delivered, its amplitude, pulse width and duration and frequencies are controlled via lines 46j-47a. If it is a burst of stimuli, the frequency and duration are controlled through the same line while a burst finished signal is sent to the microprocessor 46 via output line 47b-46k.

Programmability to the pulse generator 3 is achieved through receiver-demodulator 48 and transmitter 49. As seen, each of these devices is coupled to the microprocessor 46. The receiver-demodulator 48 and transmitter 49 are similar to those used in cardiac pacemakers.

The basic parameter settings such as sensitivity (peak voltage or slew rate), refractory, blanking, output pulse amplitude, pulse width, escape interval and ratio, escape interval to a stimulation interval, are stored in the memory of the microprocessor 46. Default values are also stored. These values can be read from memory and sent to a receiver via the transmitter.

Figure 5:
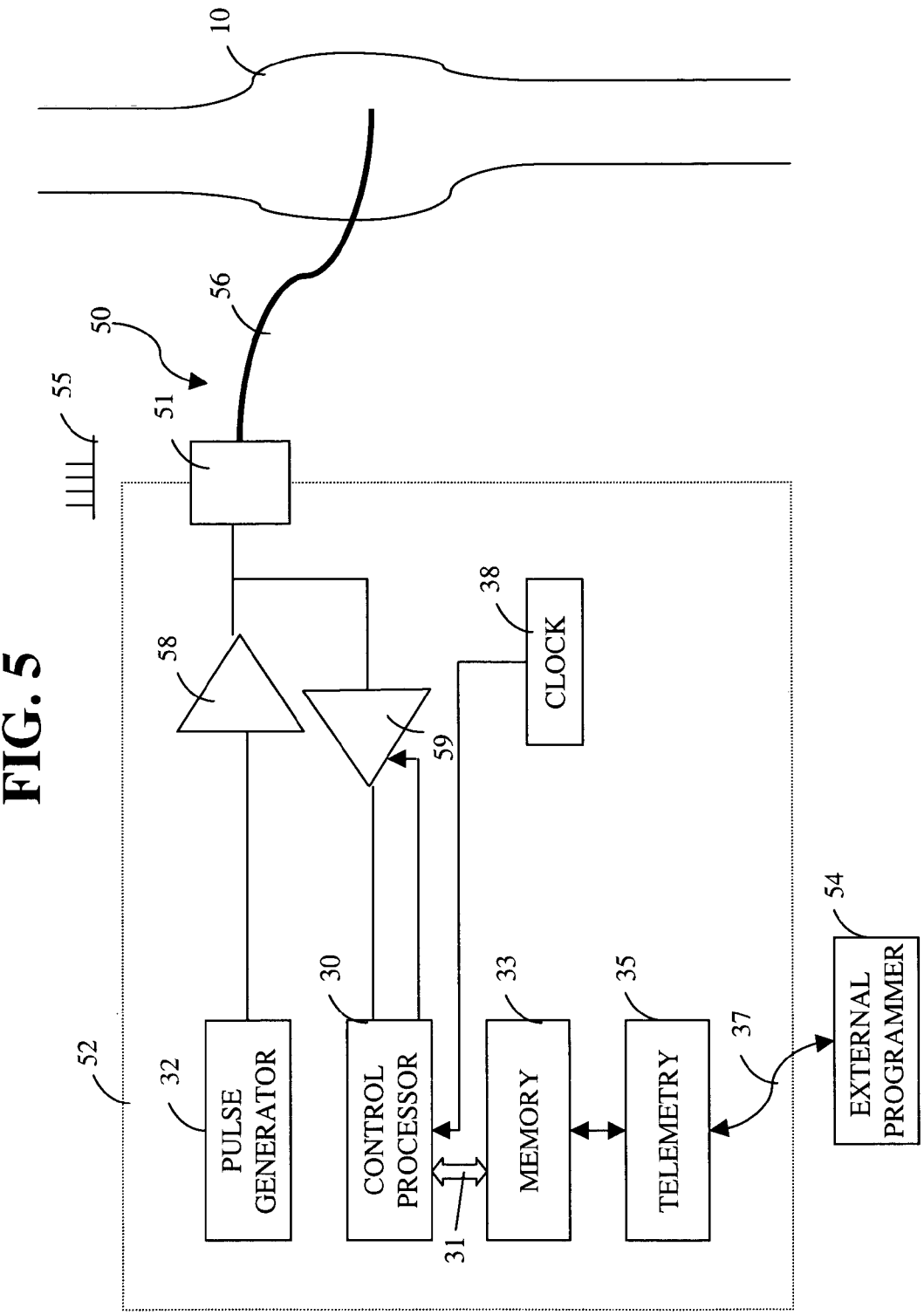
FIG. 5 shows a block diagram of another embodiment in accordance with the present invention.

FIG. 5 shows a functional block diagram of an alternate embodiment of a stimulation system 50. The stimulation system 50 includes an implantable stimulator 52, which is used in conjunction with an external programmer 54. The stimulator 52 includes an output connector 51 through which one or more medical electrical leads 56 may be connected to the internal circuits of the stimulator 52. The lead 56 is typically the Medtronic model 4300 intramuscular lead. FIG. 5 shows a single lead 56 being used to couple the stimulator 52 to the arterial wall portion 10, however, it is to be understood that the use of a single lead in this manner is only exemplary, as embodiments according to the invention may be used equally well with systems that include multiple leads that make contact with multiple locations within the vascular system or other body tissue locations.

The internal circuits of the stimulator 52 with which the lead 56 makes contact when inserted into the connector 51 include an output amplifier 58 and a sense amplifier 59. The output amplifier 58 generates electrical stimulation pulses 55 as controlled by a pulse generator 32. The pulse generator 32, in turn, receives timing signals from a control processor 30. Such timing signals control when the stimulation pulses 55 are to be generated.

A module to measure impedance or electrical resistance between electrodes (not shown) can be used to indicate a change in the muscular mass as a result of the training/stimulation of the arterial wall.

A clock circuit 38 provides the necessary clock signals for operation of the control processor 30. The control processor 30, which may be a microprocessor or equivalent processing circuit, operates in accordance with a control program that is stored in the stimulator memory 33. Also stored in the memory 33 is a set of control parameters that are used by the control program as it defines the operation of the processor 30. That is, the control parameters define the various variables associated with the operation of the stimulator, such as the duration of the escape interval, the frequency, interpulse interval, duration and amplitude of the stimulation pulses and the like. The control program specifies the particular order or sequence of events that are carried out by the processor 30. For example, the control program may specify that, upon detecting a valid intrinsic event, a control parameter stored in a particular address in the memory 33 should be retrieved in order to define an appropriate corresponding delay. The control program may further specify that if a further valid intrinsic event is sensed before the delay times out, then another control parameter stored in another location (address) of the memory 33 should be retrieved to define an appropriate delay. If a valid intrinsic event is not sensed before the timing out of the delay, then the control program may specify another memory address where a control parameter is stored that defines the amplitude and pulse width of a stimulation pulse train that is to be generated.

Of course, the above example is extremely simple, but it illustrates the basic operation of the stimulator 52. There are numerous events associated with the activity associated with a particular arterial wall, and that there are numerous types of cycles that may occur. The control or treatment program, in combination with the other control circuitry within the stimulator, thus defines how the stimulator responds to each possible event and intrinsic cycle type. The control parameters, in turn, define the magnitude of the variables associated with such response, e.g., the duration of time periods, the amplitude and widths of stimulation pulses, the gain of amplifiers, the threshold level of threshold detectors, and the like.

To add flexibility to the operation of the stimulator 52, the stimulator also includes a telemetry circuit 35. The telemetry circuit 35 allows access to the memory 33 from a remote location, e.g., from an external programmer 54 at a non-implanted location. The external programmer 54 includes means for establishing a telemetry link 37 with the telemetry circuit 35 of the implanted stimulator. Through this telemetry link 37, control parameters may be sent to the telemetry circuit 35 for storage in the memory 33. Such control parameters may thereafter be used by the control program stored in the memory 33 to steer the operation of the stimulator 52, as explained above. Additional details associated with the design and operation of a telemetry circuit 35, as well as an external programmer 54, may be found in U.S. Pat. Nos. 4,809,697 and 4,944,299, which patents are incorporated herein by reference.

In operation, the external programmer 54 is used to programmably set the control parameters associated with operation of the control processor 30. However, heretofore, the external programmer 54 has not ever been used to alter or change the control program once the stimulator has been implanted in a patient. Rather, the control program is downloaded to the memory 33 during the manufacture of the stimulator 52. In some instances, the control program is stored in read only memory (ROM), or equivalent hardwired circuitry, so that it can never to updated or changed thereafter. In other instances, it is stored in random access memory (RAM), but access to it is denied. This is done purposefully to preserve the integrity of the control program, or stated more accurately, to preserve the integrity of the function(s) controlled by the control program as well as providing the greatest amount of flexibility to permit changing of the device operation.

In contrast to the control program, which preferably is fixed, certain control parameters that define the variables used by the control program (or equivalent circuitry) in controlling the stimulator may be readily changed, from time to time, after implantation by using the external programmer 54. Thus, should there be a need to change a given control parameter, e.g., the stimulation pulse amplitude generated by the output amplifier 58, the sensitivity (threshold setting) of the sense amplifier 59, or other variables, then the appropriate control parameters that define such variables are simply updated (programmed) through the telemetry link established by the external programmer 54. Such programming of the control parameters is limited, however, so that the associated variables can only be changed within certain safe limits that are defined by the control program and/or other circuitry within the stimulator.

The memory 33 is a RAM memory that has both a control program and a set of control parameters stored therein at respective memory locations (addresses). Like conventional programmable stimulators, the set of control parameters in the memory 33 may be selectively updated (programmed), as needed, through use of the external programmer 54. The control program stored in the memory 33 may also be updated, using appropriate safeguards, through use of the external programmer 54. Thus, when new features requiring a new control program are added to the stimulator, a patient having an existing implanted stimulator can receive the benefits of such new features by simply upgrading the control program stored in his or her implanted stimulator. In this manner, the embodiment according to the invention allows an existing control program stored in an implanted stimulator to be non-invasively upgraded to a new version of the control program.

Figure 6:
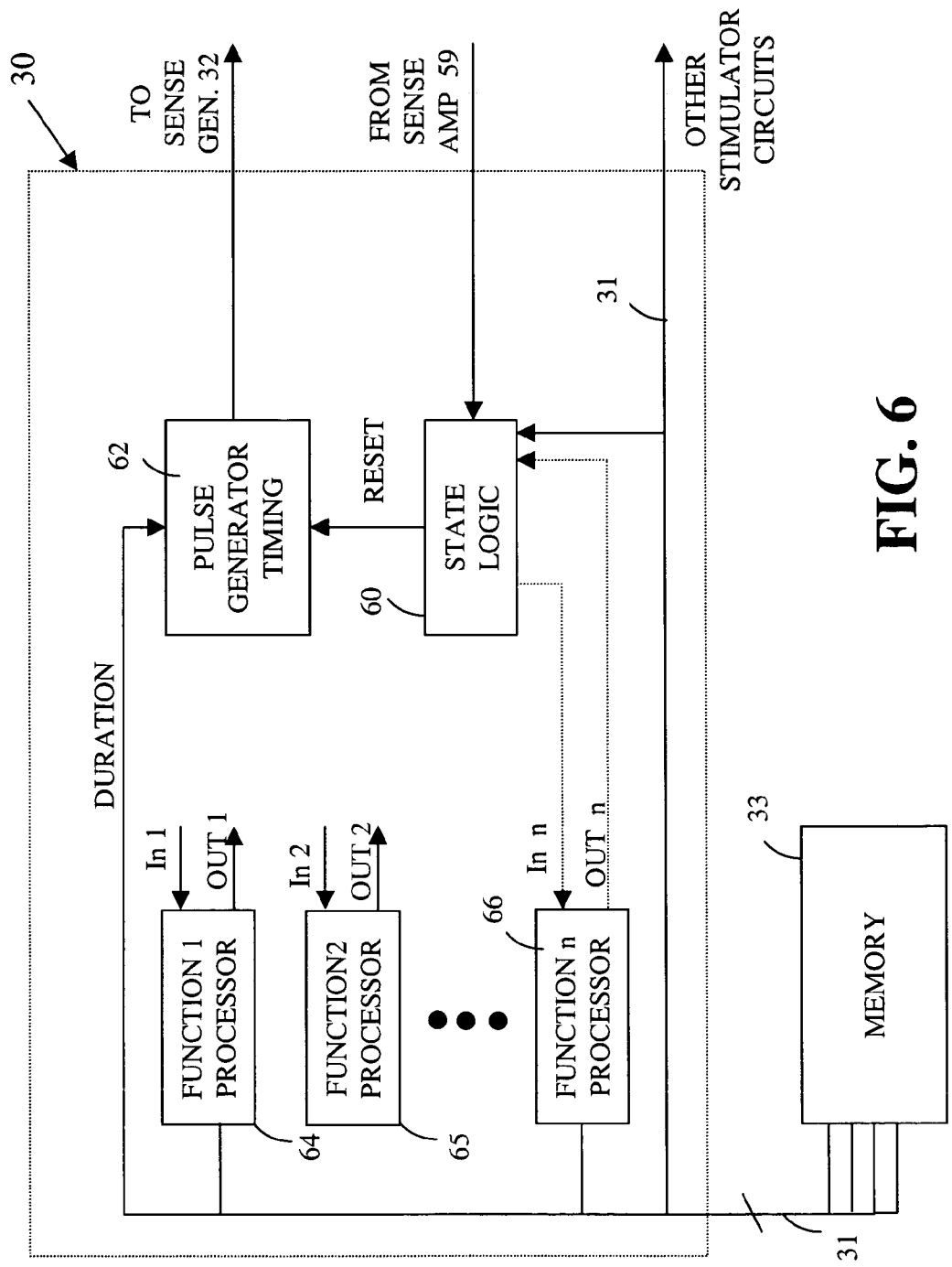
FIG. 6 is a block diagram of one embodiment of the control processor of FIG. 5.

As illustrated in FIG. 6, the control processor 30 may include multiple processors 64, 65 and 66. Each processor 64, 65 and 66 is programmed, using a respective control program stored in the memory 33, to perform a specific function associated with the operation of the stimulator 52. Such functions are supplemental to the main stimulator function, which is to monitor the arterial wall portion, or any other artery, for natural intrinsic events, and to provide stimulation pulses in the event that no natural intrinsic events are sensed, in accordance with a prescribed pacer mode. As seen an indefinite number of processors may be provided, the exact number depending upon the number of functions (locations at which these functions are) required to be performed.

State logic circuitry 60 carries out the main stimulator function, as well as the prescribed pacer mode function. The state logic circuitry 60 may be considered as a dedicated control circuit for the stimulator 52. The state logic 60 defines the state of the stimulator as a function of the input signals it receives. One such input is from the sense amplifier 59 (which may include inputs from one or all of the leads used, depending upon the particular stimulator configuration enabled). Another set of inputs to the state logic is a set of control parameters obtained from the memory 33 over a data bus 31 (see also in FIG. 5). The data bus 31 interfaces the memory 33 with the various circuits used within the stimulator. Thus, for example, a set of control parameters defines a particular operating mode for the state logic. Such operating mode dictates the particular sequence followed by the state logic, e.g., whether it operates in an inhibited or triggered mode, asynchronous, etc. Another set of control parameters defines the duration of the timing interval used by pulse generator (PG) timing circuitry 62 in controlling the various time intervals, e.g., escape intervals, used by the stimulator as it carries out its stimulation basic function.

Still other of the control parameters available on the data bus 31 are directed to the appropriate circuits that use such parameters in controlling the operation of the stimulator, e.g., the sensitivity control parameter is directed to the sense amplifier 59; the pulse amplitude and width control parameters are directed to the output amplifier 58; and so on.

The functions carried out by each of the processors 64, 65 and 66 may be varied, depending upon the particular needs of the patient. (It is to be understood that just because three processors 64, 65 and 66 are shown in FIG. 6 as part of the control processor 30, embodiments according to the invention are not so limited. The control processor 30, for the particular embodiment shown in FIG. 6, may include any number of processors, e.g., 1 to 10, that supplement the basic stimulation function carried out by the state logic 60. The functions carried out by the processors 64, 65 and/or 66 may include, e.g., the sensing and processing of physiological parameters. Further, the processors may monitor and report parameters associated with the operation of the stimulator, such as remaining battery life, the time of day, evolution of tissue electrical impedance, or overall electrical properties and the like. Indeed, the processors 64, 65, 66 . . . (however many may be used) can be used for many different types and varied functions associated with the use and operation of an implantable stimulator.

As seen in FIG. 6, the control processor 30 is effectively divided into two portions: (1) a portion that controls the basic stimulation functions, comprising the state logic 50 and the pulse generator (PG) timing circuits 62; and (2) a portion that controls the supplemental stimulation functions, comprising the processors 64, 65, and/or 66. It is to be understood that the first control processor portion, i.e., the portion that controls the basic stimulation function, could be realized using circuitry other than that shown in FIG. 6. For example, a suitable processor circuit, such as a microprocessor circuit, could readily be programmed to perform the basic stimulation function carried out by the state logic 60 and PG timing circuitry 62. Similarly, the functions carried out by the supplemental processors 64, 65 and/or 66 could likewise be achieved using specially designed hardware circuits. Indeed, any configuration of the control processor 30 that provides both supplemental and basic stimulation functions could be utilized, whether such configuration uses conventional processing circuits (e.g., microprocessors) or dedicated logic circuitry (e.g., state logic).

One of the advantages of having the control processor 30 configured as shown in FIG. 6 (to provide both the basic stimulation function and supplemental stimulation functions) is that the control programs for the supplemental stimulation function(s) can be altered (upgraded with a new program) at the same time that the basic stimulation function continues to operate. Thus, there need be no interruption in the basic stimulation function provided by the stimulator as one or more control programs are downloaded to the memory 33. As the downloading operation could take several minutes, this is an important advantage because it means the patient need not go without the therapeutic stimulation pulses provided by the stimulator.

Referring to FIG. 7, there is shown a flow chart illustrating a method 70 for providing electrostimulation to an aneurysmal sac arterial wall. The method preferably includes the step 72 of implanting leads to provide stimulation inducing the contraction of the aneurysmal sac arterial wall. Step 72 can include the step of attaching an array of leads to an interior portion or an exterior portion of the aneurysmal sac arterial wall. The method also comprises the step 74 of electrically stimulating the leads according to a treatment program preferably by emitting a stimulation pulse train at a predetermined rate suitable for the aneurysmal sac arterial wall and the step 76 of sensing a contraction condition of the aneurysmal sac. The method may further comprise the step 78 of adjusting the treatment program based on the information received from the step of sensing the contraction condition. Preferably, the adjustment step modifies the treatment program to prevent over-stimulation or over-contraction of the aneurysmal sac arterial wall.

Although a specific embodiment of the invention has been disclosed, this is done for the purposes of illustration and is not intended to be limiting with regard to the scope of the invention.

What is claimed is:

1. An aneurysmal sac arterial wall electrostimulation system, comprising:
    an array of electrical leads placeable in contact with a portion of the arterial wall to be electrostimulated;
    a treatment program for controlling said aneurysmal sac arterial wall electrostimulation stored in a memory of said system; and
    a source of electrostimulation attached to said array of electrical leads, wherein said source provides periodic electrostimulus to at least one of the array of leads in accordance with said treatment program and wherein at least one of the array of leads senses the contraction condition of the aneurysmal sac arterial wall which is provided as a feedback loop input signal to said treatment program in a matter so as to provide a controlled arterial wall contraction to offset arterial blood pressure.

2. The system of claim 1, wherein the array of electrical leads are placed on an interior portion of the arterial wall to be electrostimulated.

3. The system of claim 1, wherein the array of electrical leads are placed on an exterior portion of the arterial wall to be electrostimulated.

4. The system of claim 1, wherein the arterial wall to be electrostimulated forms a portion of the group comprising an abdominal aortic aneurysmal sac, a thoracic aortic aneurysmal sac, a ventricular aneurysmal sac, and a cerebral artery aneurysmal sac.

5. The system of claim 1, wherein the source of electrostimulation comprises a pulse generator for emitting a stimulation pulse train at a predetermined rate.

6. The system of claim 1, wherein the feedback loop input signal is used to prevent over-stimulation or over-contraction of the aneurysmal sac arterial wall.

7. A method for providing electrostimulation to an aneurysmal sac arterial wall, comprising the steps of:
    implanting leads to provide stimulation inducing the contraction of the aneurysmal sac arterial wall;
    electrically stimulating said leads according to a treatment program;
    sensing a contraction condition of the aneurysmal sac; and
    adjusting the treatment program based on the information received from the step of sensing the contraction condition.

8. The method of claim 7, wherein the step of implanting comprises attaching an array of leads to an interior portion of the aneurysmal sac arterial wall.

9. The method of claim 7, wherein the step of implanting comprises attaching an array of leads to an exterior portion of the aneurysmal sac arterial wall.

10. The method of claim 7, wherein the step of providing electrical stimulus comprises emitting a stimulation pulse train at a predetermined rate suitable for the aneurysmal sac arterial wall.

11. The method of claim 7, wherein the adjustment step modifies the treatment program to prevent over-stimulation or over-contraction of the aneurysmal sac arterial wall.

* * * * *

UNITED STATES PATENT AND TRADEMARK OFFICE
CERTIFICATE OF CORRECTION

PATENT NO.        : 7,274,960 B2                                                Page 1 of 1
APPLICATION NO.   : 10/911973
DATED             : September 25, 2007
INVENTOR(S)       : Letort et al.

It is certified that error appears in the above-identified patent and that said Letters Patent is hereby corrected as shown below:

Column 9, line 25, "ment program in a matter so as to provide a controlled" should be changed to -- ment program in a manner so as to provide a controlled --

Signed and Sealed this

Eleventh Day of November, 2008

JON W. DUDAS
*Director of the United States Patent and Trademark Office*